United States Patent [19]

Berglund et al.

[11] Patent Number: 4,695,272
[45] Date of Patent: Sep. 22, 1987

[54] DRUG RELEASE DEVICE

[75] Inventors: Bengt G. Berglund, Göteborg; Karl-Erik L. Falk, Lindome; Dan A. Magnusson, Fjäras; Nils B. Nilson, Mjölby; Ake S. Nilsson, Göteborg, all of Sweden

[73] Assignee: Aktiebolaget Hassle, Molndal, Sweden

[21] Appl. No.: 726,059

[22] Filed: Apr. 23, 1985

[51] Int. Cl.⁴ .............................................. A61M 5/00
[52] U.S. Cl. ..................................... 604/84; 604/85; 604/87; 604/252
[58] Field of Search ................................ 604/85, 80–84, 604/87, 890, 251, 252; 222/129, 145, 142.1

[56] References Cited

U.S. PATENT DOCUMENTS

| | | | |
|---|---|---|---|
| 2,129,983 | 9/1938 | Bacon | 604/251 |
| 2,659,370 | 11/1953 | Smith | 604/416 |
| 3,857,392 | 12/1974 | Ogle | 604/91 |
| 3,861,388 | 1/1975 | Vaughn | 128/214 R |
| 3,941,126 | 3/1976 | Dietrich | 604/83 X |
| 4,173,223 | 11/1979 | Raines et al. | 128/214 C |
| 4,191,183 | 3/1980 | Mendelson | 604/80 X |
| 4,392,850 | 7/1983 | Elias et al. | 604/82 |
| 4,392,851 | 7/1983 | Elias | 604/82 |
| 4,465,471 | 8/1984 | Harris et al. | 604/85 |
| 4,467,588 | 8/1984 | Carveth | 604/87 X |
| 4,474,574 | 10/1984 | Wolfe et al. | 604/85 |
| 4,534,757 | 8/1985 | Geller | 604/126 X |
| 4,606,734 | 8/1986 | Larkin et al. | 604/84 |

Primary Examiner—Stephen C. Pellegrino
Attorney, Agent, or Firm—Brumbaugh, Graves, Donohue & Raymond

[57] ABSTRACT

A drug release device for inclusion in a parenteral drug delivery system, said device comprising a chamber having an inlet for a liquid administerable to a patient by a parenteral route, a drug dissolution space within said chamber, through which said liquid can be made flow, an outlet for said liquid, and means for receiving and retaining within said drug dissolution space a drug preparation from which a drug is releasable to said liquid during such parenteral delivery, said device characterized in having means for providing the same with one or more durg release cells within which such drug preparation is initially held isolated from the liquid, each of said drug cells having means for emptying its contents of drug preparation into said drug dissolution space after insertion thereof in the drug release device.

Such device can be used for sequential emptying of a drug preparation from two or more such drug cells whereby a parenteral liquid dissolves the drug.

Also described are a parenteral drug delivery system, a drug cell, and a method of parenteral drug delivery.

13 Claims, 7 Drawing Figures

DRUG RELEASE DEVICE

TECHNICAL FIELD

The present invention is related to a drug release device, a parenteral drug delivery system containing such device and a method of parenteral administration of a drug to a patient employing such device and/or system.

The object of the invention is to provide for an improved method of drug administration via a parenteral route, notably via intravenous infusion, and to provide apparatus required for such improved method. A further object is to provide for repeated administration of two or more dosages of drug during the course of a treatment of a patient with parenteral infusion.

BACKGROUND ART

EP-AI-No. 0059694 describes a drug administration device for releasing a drug into a flow of liquid during administration by a parenteral route to a patient, such device comprising a cell having an inlet and outlet for the liquid so as to permit the liquid to flow through the cell, the cell containing a solid drug-releasing unit positioned to contact the liquid flowing through the cell in use, the drug releasing unit being adapted to release the drug at a controlled rate into the liquid. Such device is gaining interest as a valuable new concept in intravenous infusion therapy i.a. The present inventors have found that by an improvement to such device substantial advantages can be gained, and further employment in extended therapeutical fields can be made possible.

EP-AI-No. 0077604 and GB-A-No. 2107191 describe further devices for drug release to a liquid for parenteral administration.

DISCLOSURE OF THE INVENTION

The objects stated above and other objects that will be apparent are fulfilled by providing according to this invention a drug release device for inclusion in a parenteral drug delivery system, said device comprising a chamber having an inlet for a liquid administerable to a patient by a parenteral route, a drug dissolution space within said chamber through which said liquid can be made flow, an outlet for said liquid, and means for receiving and retaining within said drug dissolution space a drug preparation from which a drug is releasable to said liquid during such parenteral delivery, said device characterized in having means for providing the same with one or more drug cells within which such drug preparation is initially held isolated from the liquid, each of said drug cells having means for emptying its contents of drug preparation into said drug dissolution space after insertion thereof in the drug release device.

By parenteral administration in this context is primarily intended a prolonged administration via a needle penetrating the skin e.g. intravenously, intraarterially, intramuscularly or subcutaneously. Such administration will typically have a duration of at least a few minutes and up to several hours or days. Intravenous infusion of a drug-containing liquid and similar therapy is conceived as the major field of application.

Drug, in this context includes any agent having a beneficial effect when administered to a host suffering from disease or a healthy host, and further includes any diagnostic agent. However, as will be apparent below certain drugs are employed with special advantages according to the invention.

By a liquid administerable by a parenteral route is intended any liquid suitable for such administration. Such liquid should further have a sufficient ability to dissolve the drug to be administered. Such liquids may include saline, electrolyte, carbohydrate and other aqueous solutions as known in the art.

In certain cases the device according to the invention may contain only one cell within which the drug preparation is initially held. However, the greatest advantages with the invention will be apparent when using two or more such cells, whereby each such cell can contain a dosage unit of a drug and whereby such dosages may be consecutively released with any desired time interval into the drug dissolution space. In one preferred embodiment of the invention the device has a number of cells equal to the number of drug dosages required during a 24 hour day period. Thus, a device with e.g. 2, 3, 4, 5 or 6 cells is preferred.

According to a preferred embodiment of the invention the drug release device of the invention is characterized in that each drug cell is arranged in an outer wall of said chamber in such manner that it can be manipulated from the exterior of said chamber to empty its contents into the said space within said chamber.

The drug cells suitably have a cylindrical wall. At one end said wall is molded with a dome-shaped flexible cap extending to the exterior of the drug release device. At the opposite end said wall is connected to a releasable lid oriented to the interior of the drug release device and closing the cell in such manner that the drug contained therein will be held isolated from the interior of the device and any liquid present therein. The cell is arranged to release the releasable lid when the flexible cap is pressed. Thus, a push rod may be molded in one piece with or attached to the inside of the flexible cap, terminating near the releasable lid. Additionally, or in the alternative, pressurized air or gas or the bulk of drug within the cell can mediate the force for releasing the lid. Pressurized gas provides the advantage of giving explosive energy which secures full opening of the lid. The lid suitably have a hinge, thread or similar mechanism preventing it from falling down into the drug release device when opened.

The location of the drug cells in relation to the drug dissolution space should be chosen thus that the drug contents of each cell are completely emptied into the said space when the cell is opened. Suitably, the drug cells are placed in symmetric orientation to each other above the drug dissolution space.

The releasable lid may be replaced with a breakable membrane in certain instances, e.g. when the drug preparation in the cell is in liquid form.

The drug cells per se constitute a further aspect of this invention.

The drug cells may be firmly attached to the drug release device or insertable therein and/or releasable therefrom. Thus, the drug release device may be provided with means for introducing a drug cell through an outer wall thereof. Such means may e.g. be a threaded cylindrical aperture designed to receive and engage with a cylindrical drug cell having corresponding threads, or an aperture adapted to receive a drug cell by a snap-fit mechanism. A gasket or similar means may be provided to ensure a tight connection between the cell and the body of the drug release device. To prevent contamination of the interior of the device a releasable outer cover or lid may be provided covering the aperture. For a similar purpose an inner cover or lid may further be provided which is releasable either by the action of introducing the drug cell or by the action of releasing the releasable lid of the drug cell. Such inner cover or lid additionally may have the function of maintaining the pressure relative to the environment while introducing a drug cell during the course of parenteral liquid administration to a patient. The outer and inner covers or lids, like the releasable lid of the drug cell, may be a rigid plastic lid or a flexible cover e.g. an aluminium foil cover. The drug cells may be provided in a releasable outer casing protecting the cells from contamination before use. Such outer casing may e.g. be a blister pack.

According to another preferred embodiment of the invention the drug release device is characterized in being suspendable in a vertical position wherein the inlet is in an upper part of said chamber and the space within which the drug preparation is to be received is in a lower part of said chamber. In a preferred form of such a device the inlet terminates in a drip delivering tube extending into the chamber. Thus, the device of the invention will additionally function as a drip chamber as used in conventional infusion systems. The infusion rate may thus be monitored by the drip rate and controlled, such monitoring and control being done manually or by automatic means.

Suitably the device according to the invention has a filter covering the outlet thereof to stop drug particles as well as other undesired matter from leaving the device and entering into the patient's body. According to a preferred embodiment of the invention the device is characterized in that said filter extends into the space within which the drug preparation is to be received in such manner that the drug preparation will not entirely cover the filter until the contents of all drug cells are emptied into said space.

The filter employed should have a mesh size known as suitable in the art. If desired the filter may have a sufficiently small mesh size to give sterile filtration. Typically a mesh size giving sterile filtration is about 0.22 μm. In certain cases about 0.45 μm is a suitable mesh size.

In designs where the filter is shaped as or enclosed in a hollow body it may be desirable to provide said body with air vent means. This may be done e.g. by including in the upper part of such body a so called hydrophobic filter, i.e. a filter that can be penetrated by air but not by an aqueous liquid.

To improve the flow of liquid through the drug preparation the drug dissolution space may have means for establishing a flow path through the preparation. Such means may e.g. be a hub covering the filter or a plate or screen for supporting the preparation above the filter.

Another aspect of the invention is a parenteral drug delivery set comprising a drug release device as defined above and means for connecting the inlet and outlet thereof to a container for liquid and to a parenteral needle, respectively. Any kind of connection means known in the art, including quick couplings, can be used to connect different parts of the parenteral drug delivery set.

Thus, the inlet is suitably provided with a spike which in the use position of the device is in the upper part thereof and which is used to penetrate a membrane of a liquid container, such as a bottle or plastic bag. The outlet is connectable via tubing to a parenteral needle such as an infusion cannula. The parenteral drug delivery set should be provided with flow control equipment, e.g. an adjustable clamp on the tubing. Said tubing may further be provided with ports to enable piggyback or parallel connection of the set with one or more parenteral sets either sets according to this invention or different sets. A separate drip chamber may be interposed in the set when the drug release device is designed without a drip delivering tube or when an additional drip monitoring device is desired, e.g. for compatibility with available automatic control equipment. Further two or more drug release devices may be connected in series. Tubing enabling liquid to pass by the device can be provided either outside or inside the device, such tubing provided when required with closure and control means for the bypass liquid.

The drug preparation to be used in the drug release device is preferably in solid form, e.g. in the form of granules, pellets, tablets or powder. Among solid drug preparations to be used are preparations giving controlled release of the drug as further described in EP-AI-No. 0059694. By employing such preparations the drug release device, having several drug cells, can provide for continous drug administration over a long time. However, the device is advantageous also in employing non-controlled release forms, e.g. when repeated drug administration having a relatively short duration is desired during the course of liquid infusion for an extended period of time, as may be the case when e.g. antibiotics are administered. In the alternative the drug preparation may be a liquid preparation.

One concept of the invention is employing the same drug preparation in all drug cells. Another concept is employing different drugs or different dosages of drugs in different drug cells, thus enabling sequential administration of such different drugs or dosages. In such cases, the visible part of the drug cells may be provided with appropriate symbols for drugs and/or dosages.

A method of parenteral drug delivery is a further aspect of the invention.

The invention is further described with reference to the appended drawings wherein.

Figures 1, 2:
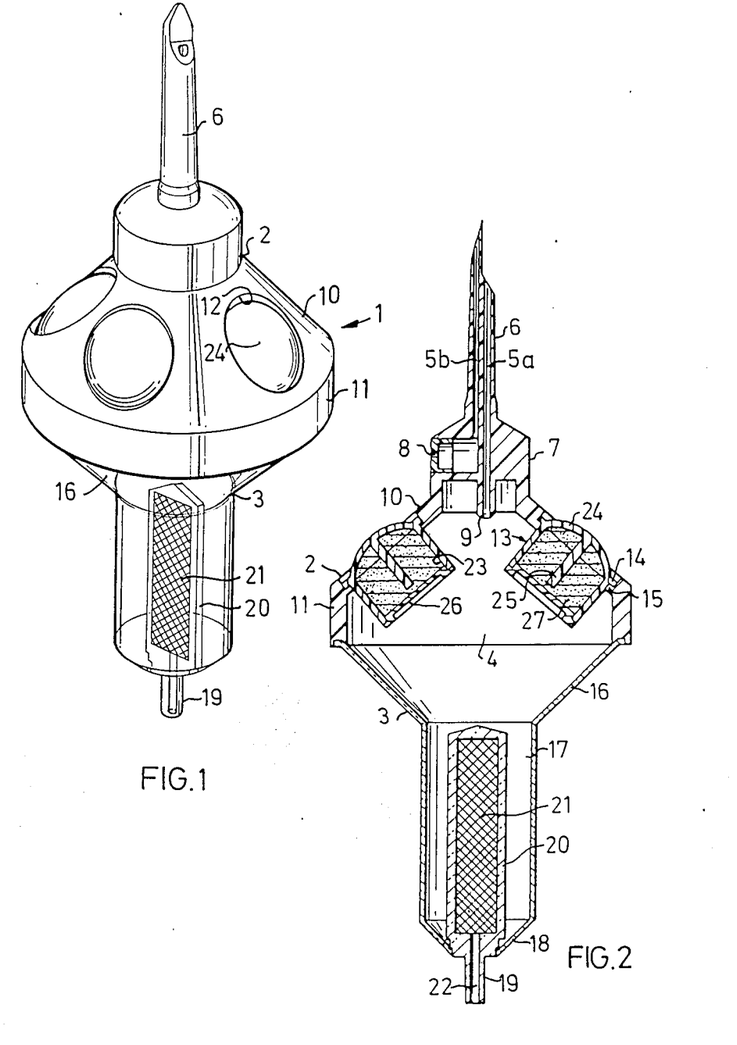
FIG. 1 is a perspective view of a drug release device according to the invention.
FIG. 2 is a longitudinal section of the device in FIG. 1.

In the drawing 1 denotes a drug release device comprising an upper part 2 and a lower part 3 defining between them a chamber 4. In the upper part 1 is arranged an inlet channel 5a for a liquid, said channel going through a spike 6, which can be used to penetrate a closure membrane of a container for the liquid, and further through a top cylindrical portion 7. Through the spike further goes an air vent channel 5b terminating at its lower end in a cavity provided with a hydrophobic filter·air inlet 8. The lower end of the inlet channel 5a terminates in a drip delivering tube 9.

The upper part 2 of the device has a top cylindrical portion, a flared conical portion 10 and a cylindrical base portion 11. Through the wall of said conical portion four circular openings 12 extend. Through each opening a drug cell 13 is inserted resting by means of a flange 14 against an edge 15 in the opening. To the lower end of the cylindrical portion the lower part 3 is attached at a conical portion 16 thereof continuing into a cylindrical portion, whereby a drug dissolution space 17 is formed by the walls of the lower part 3. Through an end wall 18 of the lower part an outlet tube 19 for liquid extends. Said outlet tube is integral with a frame 20 covered on both sides with a filter screen 21. The space between the screens communicates via an outlet channel 22 with the exterior of the drug release device.

Each drug cell 13 consists of a cylindrical wall 23 molded with a convex cap 24 and a push rod 25 extending axially inside the cell terminating near a releasable lid 26 closing against the wall 23, which lid will pop open when the cap 24 is pushed.

When the lid is opened, a drug preparation 27 will fall down into the space 17. When the lower part is previously filled with liquid to a desired level the drug may either sink to the bottom of space 17, float on the liquid surface or be suspended in the liquid, depending on density relation i.a. A solid drug preparation having a substantially greater density than the liquid will fall down between the cylindrical wall and the filter frame 20 or filter 21. Once in contact with the liquid the drug preparation will start releasing its drug contents into the liquid. Provided a liquid flow has been established through the drug release device, the drug solution thus formed will leave the device through the outlet channel 22.

All parts of the device are suitably made of appropriate plastic materials known in the art, whereby at least the lower part is preferably made of transparent material. Said lower part 3 is further preferably made with flexible walls so that it may be squeezed to help establish a desired liquid level 28 within the device.

Figure 3:
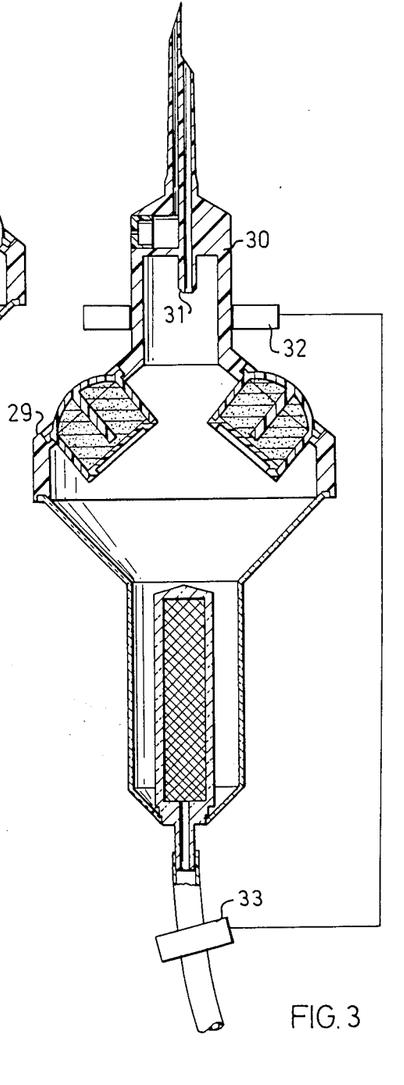
FIG. 3 is a longitudinal section of a drug release device according to another embodiment of the invention.

In the drug release device shown in FIG. 3 the upper part 29 has a long cylindrical section 30 made of transparent material through which drip rate from a drip delivering tube 31 can be monitored the eye of an attendant who controls the flow rate manually or by an automatic monitoring device shown schematically at 32 connected to an automatic flow control device shown schematically at 33. The other parts of the device in FIG. 2 are similar to the corresponding parts of the device in FIG. 1.

Figure 4:
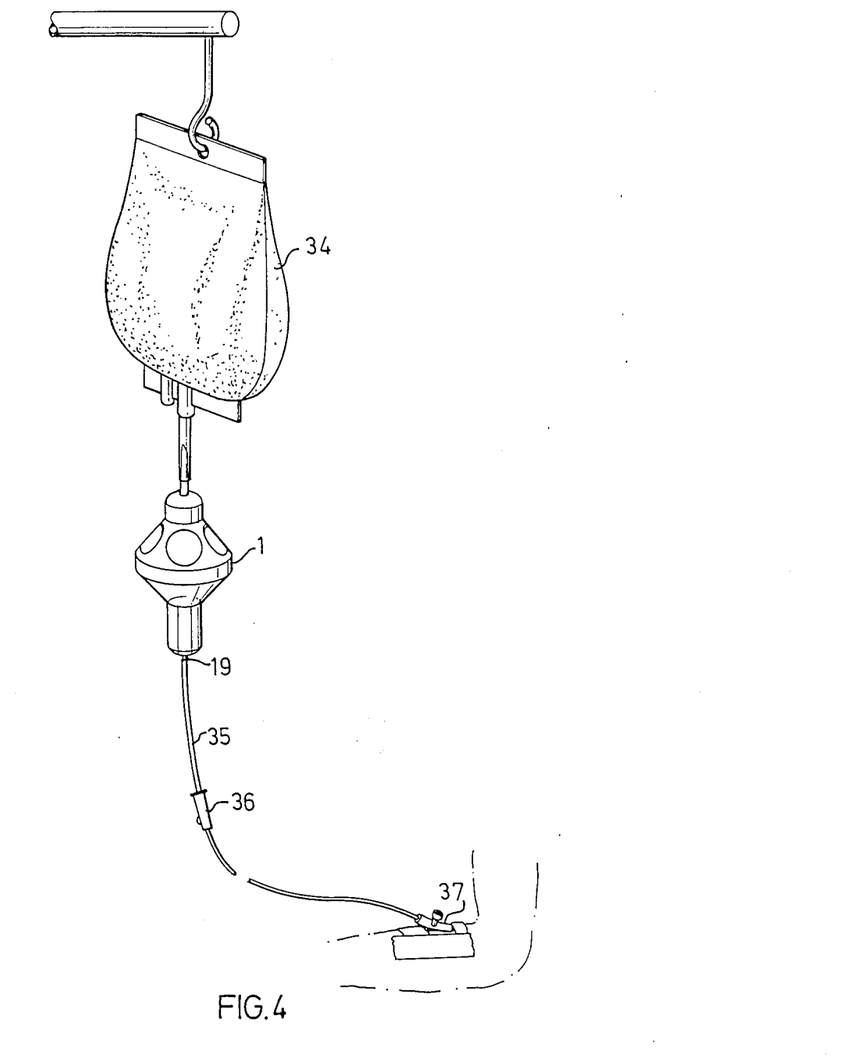
FIG. 4 is a view of a parenteral drug delivery system comprising a drug release device of the invention.

In FIG. 4 the drug release device 1 is shown connected via spike 6 to a plastic bag container 34 for an infusion liquid. The outlet tube 19 is connected at one end to a flexible infusion tube 35 provided with a flow control clamp 36. The opposite end of the tube is connected to an infusion cannula 37 inserted into the arm of a patient.

Figure 5:
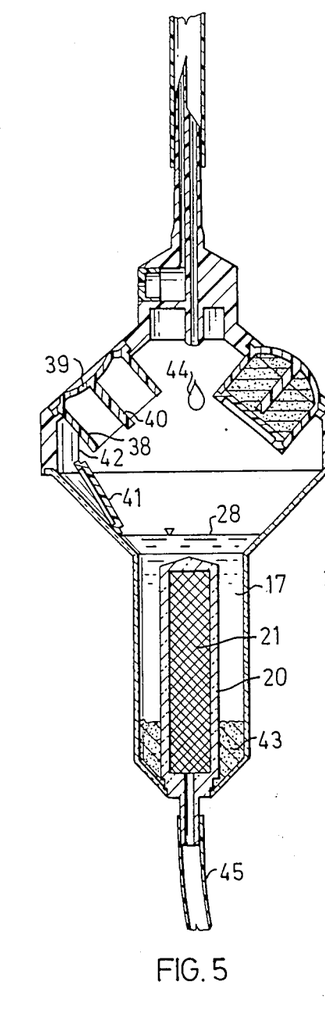
FIG. 5 is a longitudinal section of the device in FIGS. 1 and 2 shown after release of one drug cell.

In FIG. 5 one drug cell 38 is opened by pressing its cap 39 inwards whereby the push rod 40 has forced the lid 41 to open. Lid 41 remains hanging from the drug cell at the lowest part thereof by a hinge-like molded material piece 42 connecting those parts. A granular drug preparation 43 initially held in the drug cell has been emptied into the drug dissolution space 17 and has fallen to the bottom of said space at the sides of the filter frame 20 and filter 21. A liquid level 28 is established below the opened lid of the drug cell 37. As liquid flows dripwise at 44 into the device liquid, with dissolved drug is let out via a tube 45.

Figure 6:
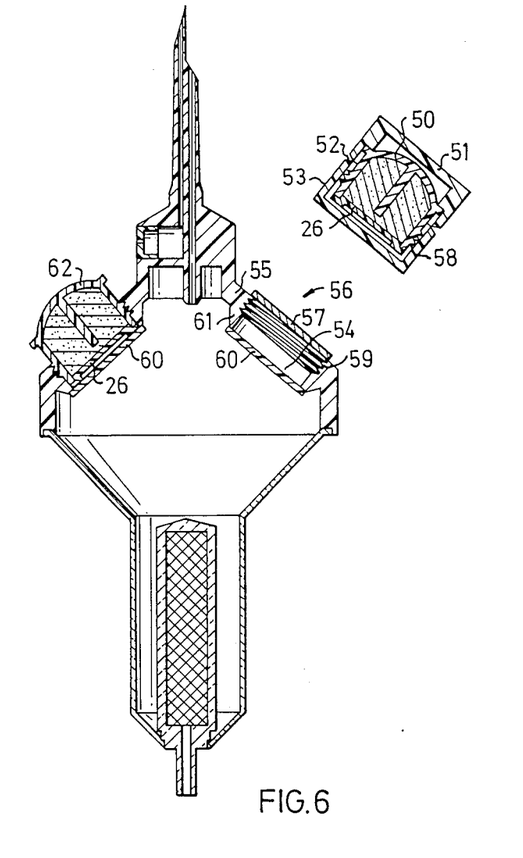
FIG. 6 is a longitudinal section of a drug release device having means for insertion of a drug cell therein.

In FIG. 6 a cylindrical drug cell 50 is shown, enclosed in an outer protective casing 51 provided with a weakening grove 52 at which the protective casing may be broken and the lower part 53 thereof removed. The remainder of the protective casing may optionally be designed for removal before or after insertion of the drug cell. The drug cell 50 is arranged to be received in an aperture 54 in the upper part 55 of a drug release device 56, said aperture being covered and sealed by an outer lid 57 attached by means of adhesive material, and releasable before insertion of the drug cell. The drug cell has threads 58 which will engage with corresponding threads 59 in the aperture. An inner lid 60 is attached covering the aperture on the inside. Said inner lid rests on a collar 61 shaped from the wall of the upper part 55 of the device in such manner that it permits insertion of a drug cell. When the releasable lid 26 is opened, as previously described, the inner lid 60 will simultaneously open. By employing a shorter collar the lid may be opened on insertion of the drug cell.

A second drug cell 62 is shown inserted in position through the wall of the drug release device with the releasable lid 26 and the inner lid 60 still in closed position.

Figure 7:
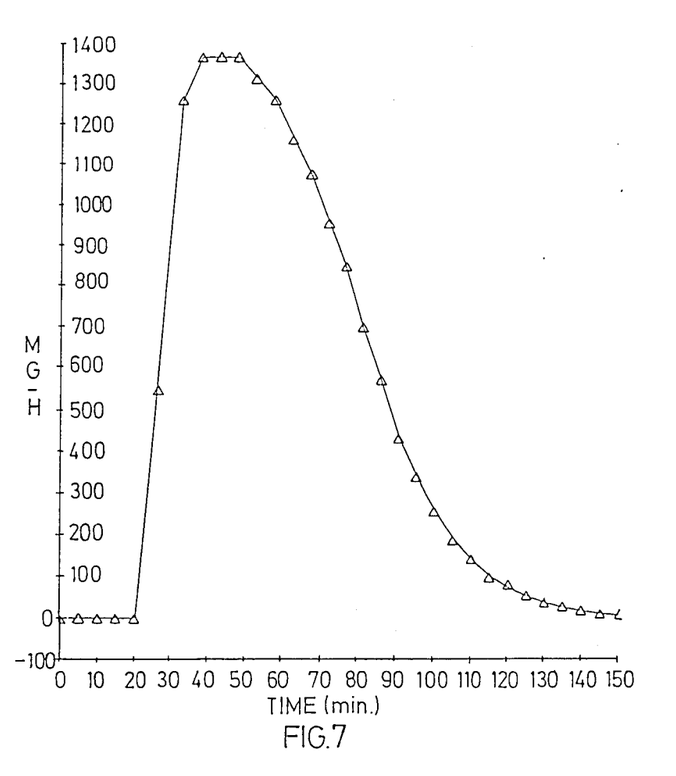
FIG. 7 is a diagram showing drug release from a drug release device of the invention.

The diagram in FIG. 7 shows rate of potassium chloride release from a device of the invention activated by releasing the contents of one drug cell at time 20 minutes, such cell containing 1312.5 mg KCl. The infusion liquid was 0.9% aqueous NaCl solution at a temperature of 25° C.

We claim:

1. A drug release device for inclusion in a parenteral drug delivery system comprising a chamber having an outer wall, an inlet for a liquid administerable to a patient by a parenteral route and an outlet for liquid containing dissolved drug, the wall, inlet and outlet together defining a drug dissolution space within said chamber through which said liquid will flow during such parenteral delivery, and means for receiving and retaining within said drug dissolution space a drug preparation from which a drug is releaseable to said liquid during such parenteral delivery.

the improvement comprising providing one or more drug cells disposed on the outer wall of said chamber, each cell containing said drug preparation which is held isolated from the liquid by said cell, each of said drug cells having means for emptying its contents into said drug dissolution space.

2. A drug release device as claimed in claim 1 characterized in that the drug cells are firmly attached to the device.

3. A drug release device as claimed in claim 2, characterized in that each drug cell is arranged in an outer wall of said chamber in such manner that it can be manipulated from the exterior of said chamber to empty its contents into the said space within said chamber.

4. A drug release device as claimed in claim 2, characterized in being suspendable in a vertical position wherein the inlet is in an upper part of said chamber and the space within which the drug preparation is to be received is in a lower part of said chamber.

5. A drug release device as claimed in claim 1 characterized in that the drug cells are insertable in said drug release device.

6. A drug release device according to claim 5, characterized in being provided with means for introducing a drug cell through an outer wall thereof.

7. A drug release device according to claim 6, characterized in that such means is a cylindrical aperture.

8. A vertically suspendable drug release device for inclusion in a parenteral drug delivery system comprising a chamber having an outer wall, an inlet for a liquid administerable to a patient by a parenteral route, said inlet, which is located in an upper part of said chamber, terminating in a drip delivering tube extending into said chamber, and an outlet for liquid containing dissolved drug, the wall, inlet and outlet together defining a drug dissolution space within said chamber through which said liquid will flow during such parenteral delivery, said drug dissolution space being located in a lower portion of said chamber, and means for receiving and retaining within said drug dissolution space a drug preparation from which a drug is releasable to said liquid during such parenteral delivery, the improvement comprising providing one or more drug cells disposed on and firmly attached to the outer wall of said chamber, each cell containing said drug preparation which is held isolated from the liquid by said cell, each of said cells having means for emptying its contents into said drug dissolution space.

9. A vertically suspendable drug release device for inclusion in a parenteral drug delivery system comprising a chamber having an outer wall, a spike containing an inlet for a liquid administerable to a patient by a parenteral route, said spike being in an upper part of the drug release device and adapted to pierce a membrane of a container for liquid, and an outlet for liquid containing dissolved drug, the wall, inlet and outlet together defining a drug dissolution space within said chamber through which said liquid will flow during such parenteral delivery, said drug dissolution space being located in a lower portion of said chamber, and means for receiving and retaining within said drug dissolution space a drug preparation from which a drug is releasable to said liquid during such parenteral delivery, the improvement comprising providing one or more drug cells disposed on and firmly attached to the outer wall of said chamber, each cell containing said drug preparation which is held isolated from the liquid by said cell, each of said cells having means for emptying its contents into said drug dissolution space.

10. A drug release device for inclusion in a parenteral drug delivery system comprising a chamber having an outer wall, an inlet for a liquid administerable to a patient by a parenteral route and an outlet for liquid containing dissolved drug, the wall, inlet and outlet together defining a drug dissolution space within said chamber through which said liquid will flow during such parenteral delivery, and means for receiving and retaining within said drug dissolution space a drug preparation from which a drug is releasable to said liquid during such parenteral delivery, the improvement comprising providing one or more drug cells disposed on the outer wall of said chamber, each cell containing said drug preparation which is held isolated from the liquid by said cell, each of said drug cells having means for emptying its contents into said drug dissolution space and having a filter covering said outlet of said chamber which extends into said drug dissolution space in such a manner that said drug preparation will not entirely cover said filter until the contents of all of said drug cells have been emptied into said drug dissolution space.

11. A method of parenteral drug delivery to a host in need of such drug delivery comprising administering to such host a liquid suitable for parenteral drug delivery by means of a parenteral drug delivery system comprising a drug release device, wherein said drug release device comprises a chamber having an outer wall, an inlet for a liquid administerable to a patient by a parenteral route and an outlet for liquid containing dissolved drug, the wall, inlet and outlet together defining a drug dissolution space within said chamber through which said liquid will flow during such parenteral delivery, and means for receiving and retaining within said drug dissolution space a drug preparation from which a drug is releaseable to said liquid during such parenteral delivery, the improvement comprising providing one or more drug cells disposed on the outer wall of said chamber, each cell containing said drug preparation which is held isolated from the liquid by said cell, each of said drug cells having means for emptying its contents into said drug dissolution space comprises a chamber disposed on the outer wall of said chamber, each cell containing said drug preparation which is held isolated from the liquid by said cell, each of said drug cells having means for emptying its contents into said drug dissolution space, and during said administration of liquid emptying the contents of at least one of said drug cells into said drug dissolution space, whereby said contents are dissolved in said liquid which is flowing through said dissolution space.

12. A drug release device for inclusion in a parenteral drug delivery system comprising a chamber having an outer wall, an inlet for a liquid administerable to a patient by a parenteral route and an outlet for liquid containing dissolved drug, the wall, inlet and outlet together defining a drug dissolution space within said chamber through which said liquid will flow during such parenteral delivery, and means for receiving and retaining within said drug dissolution space a drug preparation from which a drug is releaseable to said liquid during such parenteral delivery, the improvement comprising providing one or more drug cells holding therein a drug preparation isolated from the liquid disposed on and firmly attached to the outer wall of said chamber, said drug cells having a cylindrical wall, a dome-shaped flexible cap at one end of said wall and a releaseable lid at the opposite end of said wall, the cylindrical wall, cap and lid together defining a lumen for holding said drug preparation, the cap having a push-rod extending through said lumen to a position near the releaseable lid, such that when the cap is pressed from the outside, said lid of said drug cell is released and said drug preparation contained in said drug cell is emptied into said drug dissolution space to mix with said liquid flowing through said space.

13. A parenteral drug delivery set comprising a drug release device as claimed in any one of claims 1, 2 to 4, 5 to 7, 8–10 or 12, a container for liquid in communication with the inlet thereof and a parenteral needle in communication with the outlet thereof.

* * * * *

UNITED STATES PATENT AND TRADEMARK OFFICE
CERTIFICATE OF CORRECTION

PATENT NO. : 4,695,272

DATED : September 22, 1987

INVENTOR(S) : Berglund et al.

It is certified that error appears in the above-identified patent and that said Letters Patent is hereby corrected as shown below:

Title page, following Item 22, insert: --[30] Foreign Application Priority Data Oct. 26, 1984 Sweden ..... 8405385-9 Apr. 1, 1985 Sweden ..... 8501593-1--.

Signed and Sealed this

Fifteenth Day of March, 1988

Attest:

DONALD J. QUIGG

Attesting Officer

Commissioner of Patents and Trademarks